United States Patent
Herickhoff et al.

(10) Patent No.: US 8,202,558 B2
(45) Date of Patent: *Jun. 19, 2012

(54) REPRODUCTIVE CELL FUNCTION PRESERVATION SYSTEM

(75) Inventors: Lisa Ann Herickhoff, Fort Collins, CO (US); James August Herickhoff, Fort Collins, CO (US)

(73) Assignee: Membrane Protective Technologies, Inc., Fort Collins, CO (US)

( * ) Notice: Subject to any disclaimer, the term of this patent is extended or adjusted under 35 U.S.C. 154(b) by 320 days.

This patent is subject to a terminal disclaimer.

(21) Appl. No.: 12/590,773

(22) Filed: Nov. 13, 2009

(65) Prior Publication Data

US 2010/0068809 A1    Mar. 18, 2010

Related U.S. Application Data

(63) Continuation of application No. 11/397,112, filed on Apr. 4, 2006, now Pat. No. 7,622,143.

(60) Provisional application No. 60/668,224, filed on Apr. 5, 2005.

(51) Int. Cl.
    *A61K 36/00*      (2006.01)

(52) U.S. Cl. .................... 424/777; 424/725

(58) Field of Classification Search ............... None
See application file for complete search history.

(56) References Cited

U.S. PATENT DOCUMENTS

2005/0214394 A1   9/2005   Dao et al.

FOREIGN PATENT DOCUMENTS

| CN | 1207920 | 2/1999 |
| CN | 1303689 | 7/2001 |
| DE | 4431393 | 2/1996 |
| RU | 2106859 | 3/1998 |
| RU | 2120272 | 10/1998 |
| RU | 2123320 | 12/1998 |
| RU | 2129423 | 4/1999 |
| RU | 2132183 | 6/1999 |
| RU | 2134570 | 8/1999 |

OTHER PUBLICATIONS

Baker M. and Aitken R.J., "The Importance of Redox Regulated Pathways in Sperm Cell Biology", Molecular and Cellular Endocrinology 216:47-54 (2004).
Soberman, R.J., "The Expanding Network of Redox Signaling: New Observations, Complexities, and Pperspectives", The Journal of Clinical Investigation 111(No. 7):571-574 (2003).
Kirk, et al. "Comparison of In Vitro Laboratory Analyses with the Fertility of Cryopreserved Stallion Spermatozoa", Theriogenology 64: 1422-1439 (2005).
J.J. Parish "Capacitation of Bovine Sperm by Heparin" 38 Biology of Reproduction 1171 (1988).
Ambaye aet al., Effect of *Hippophae salicifolia* DD. Don on Reproductive Organs of Male Rats, Indian Journal Exp. Biology, vol. 3, Jul. 1965.

(Continued)

*Primary Examiner* — Christopher R. Tate
*Assistant Examiner* — Deborah A. Davis
(74) *Attorney, Agent, or Firm* — Craig R. Miles; CR Miles, P.C.

(57) ABSTRACT

Compositions or extracts (2)(15)(24)(25)(16)(23)(31)(36)(41) obtained from the fruit (4) or leaves (26) of plants of the genus *Hippophae* (1) and methods of using such compositions or extracts to reduce loss of reproductive cell function.

17 Claims, 1 Drawing Sheet

OTHER PUBLICATIONS

Thomas, S.C., Chapter 2. Taxonomy, Natural Distribution, and Botany, Pacific Agri-Food Research Center, 2003, pp. 7-8 and 54-55, NRC Research Press, Ottawa Canada.

Mustafa Numan Bucak, et al., Effect of anti-oxidants and oxidative stress parameters on ram semen after the freeze-thawing process, Small Ruminant Research 75, 2008, pp. 128-34, ScienceDirect.

Cassani, Paula, et al., Relationship between total superoxide dismutase activity with lipid peroxidation, dynamics and morphological parameters in canine semen, Animal Reproduction Science 86, 2005, pp. 163-173, Elsevier.

Chenoweth, P.J., Influence of the male on embryo quality, Theriogenology 68, 2007, pp. 308-315, ScienceDirect.

The clinical utility of sperm DNA integrity testing, The Practice Committee of the American Society for Reproductive Medicine, Fertility and Sterility, vol. 86, Suppl. 4, Nov. 2006, pp. S35-S37, Elsevier Inc.

Donnelly, Eilish T., et al., Antioxidant supplementation in vitro does not improve human sperm motility, Fertility and Sterility, vol. 72, No. 3, Sep. 1999, pp. 484-495, Elsevier Science Inc., USA.

Faxcroft, G.R., et al., Identifying useable semen, Theriogenology 70, 2008, pp. 1324-1326, ScienceDirect.

Fujihara, Noboru, et al., Prevention of the Production of Lipid Peroxide in Rooster Spermatozoa, Animal reproduction Science 7, 1984, pp. 385-390, Elsevier Science Publishers, Netherlands.

Koa, Shu-Huei, et al., Increase of oxidative stress in human sperm with lower motility, Fertility and Sterility, vol. 89, No. 5, May 2008, pp. 1183-1190, Elsevier Inc.

O'Brien, Jeanne, et al., Sperm DNA Integrity and Male Infertility, Urology 65, 2005, pp. 16-22, Elsevier Inc.

Meseguer, Marcos, et al., The significance of sperm DNA oxidation in embryo development and reproductive outcome in an oocyte donation program: a new model to study a male infertility prognostic factor, Fertility and Sterility, vol. 89, No. 5, May 2008, pp. 1191-1199, Elsevier Inc.

Morte, Maria Ines, et al., The quantification of lipid and protein oxidation in stallion spermatozoa and seminal plasma: Seasonal distinctions and correlations with DNA strand breaks, classical seminal parameters and stallion fertility, Animal reproduction Science 106, 2008, pp. 36-47, Elsevier.

Potts, R.J., et al., Seminal plasma reduces exogenous oxidative damage to human sperm, determined by the measurement of DNA strand breaks and lipid peroxidation, Mutation Research 447, 2000, pp. 249-256, Elsevier Science.

Tavilani, Heidar, et al., Malondialdehyde levels in sperm and seminal plasma of asthenozoospermic and its relationship with semen parameters, Clinica Chimica Acta 356, 2005, pp. 199-203, Elsevier.

Hyvonen, Jaakko, On phylogeny of Hippophae (*Elaeagnaceae*), Nordic Journal of Botany, 1995, pp. 51-63.

Li T.S.C. and Beveridge, Sea Buckthron (*Hippophae rahamonides L.*), Production and Utilization, NRC Research Press, 2003.

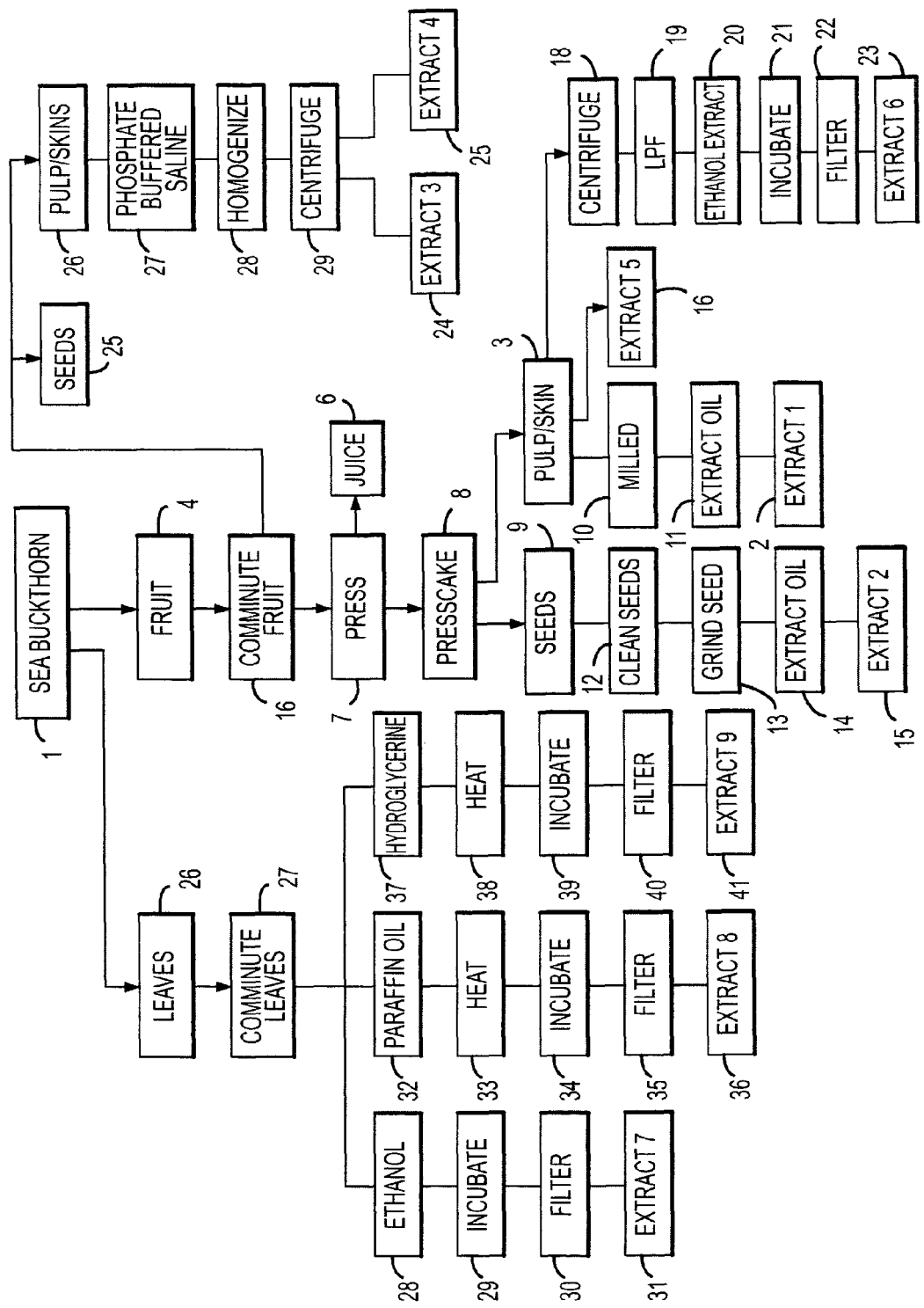

REPRODUCTIVE CELL FUNCTION PRESERVATION SYSTEM

This United States Patent Application is a continuation of U.S. patent application Ser. No. 11/397,112, filed Apr. 4, 2006, which claims the benefit of U.S. Provisional Patent Application No. 60/668,224, filed Apr. 5, 2005, each hereby incorporated by reference herein.

I. TECHNICAL FIELD

Compositions or extracts obtained from plants of the genus *Hippophae* and methods of using such compositions or extracts to reduce loss of reproductive cell function.

II. BACKGROUND

Sea Buckthorn (genus *Hippophae*) can be used for a variety of purposes including, for example, the unsaturated fatty acids of Sea Buckthorn seed oil to regulate blood lipids, resist angiosclerosis and radiation, restrain tumor cell growth, strengthen immunity, and nourish the skin as described in CN1207920 (1999); the oil from Sea Buckthorn fruits in cosmetic, pharmaceutical, and food products as described in DE4431393 (1996)); the oil extract of Sea Buckthorn for skin care products as described in RU2106859 (1998)); the oil of Sea Buckthorn in cosmetic cream as described by RU2134570 (1999)); an ointment containing Sea Buckthorn (0.5-1.5%) for suppressing caragenin-induced edemas and passive cutaneous anaphylaxis in patients with inflammatory and allergic skin damages as described by RU2132183 (1999); an ointment containing Sea Buckthorn oil for treatment of burns and infected injuries as described by RU2129423 (1999); a cosmetic cream containing Sea Buckthorn oil to protect facial skin in winter as described by RU2120272 (1998); and a cream containing Sea Buckthorn oil showing anti-allergic, bactericidal, anti-inflammatory, regenerative activities as described by RU2123320 (1998); and extracts of Sea Buckthorn as a cancer therapies as described by US2005/0214394.

Even though a numerous and wide variety of applications have been described for Sea Buckthorn, these applications do not appear to include compositions or extracts or methods of using compositions or extracts obtained from plants of the genus *Hippophae* administered to or combined with reproductive cells. A substantial problem with the manipulation of reproductive cells (as defined below) in vitro can be a significant loss of in vivo reproductive cell characteristics such as alteration of the lipid bilayer, alteration of cellular organelles, cell apoptosis, or cell necrosis, or decreased motility of sperm cells.

In particular, sperm cells contain a relative lack of cytosolic antioxidant enzymes, but are redox active cells and generate significant levels of reactive oxygen species (ROS) during normal cellular events including motility, capacitation, acrosome reaction and sperm-oocyte fusion. See Baker M. and Aitken R. J., "The Importance of Redox Regulated Pathways in Sperm Cell Biology", Molecular and Cellular Endocrinology 216:47-54 (2004). Oxidation can be a particularly damaging event because it often initiates a cascade event. For example, exterior oxidation (oxidation of the lipid bilayer surrounding the cell), can result in internal cellular damage via oxidation of the lipid bilayer and production of reactive intermediates that cause oxidation of internal organelle membranes, proteins and DNA. Soberman, R. J., "The Expanding Network of Redox Signaling: New Observations, Complexities, and Perspectives", The Journal of Clinical Investigation 111(Number 7):571-574 (2003). Reactive intermediates (oxidants), or ROS include superoxide, hydrogen peroxide ($H_2O_2$), hydroxy radial, and singlet oxygen. Interestingly, the function of ROS is dichotomous, for both oxidation and reduction are important in regular cell functioning and signaling. ROS exposure allows cells to initiate maturation events and protective pathways but unfortunately also initiates premature acrosome reactions, apoptosis (cell death) or necrosis when stress and damage becomes too great.

The loss of such in vivo reproductive cell characteristics can result in decreased fertility or decreased viability of the reproductive cells, or both. A decrease in the viability or fertility of reproductive cells can be a significant disadvantage in the context of the preparation, cooling, freezing, cooled or frozen storage, thawing or thawed storage of sperm cells contained in artificial insemination straws (or other containers or vessels), the artificial insemination of animals; the preparation, manipulation, cooling, freezing, cooled or frozen storage, the thawing or thawed storage of oocytes; the in vitro fertilization of oocytes; or the like.

This problem can be further exacerbated in the context of recent advances in the flow analysis or the flow sort of sperm cells to obtain sex selected populations of sperm cells (populations of sperm cells bearing predominantly an X-chromosome or a Y-chromosome). Because flow analyzed or flow sorted sperm cells undergo an increased number of manipulations to stain the nuclear DNA, to flow analyze, flow sort and collect the desired number of sperm cells, the resulting flow sorted sperm cells collected have an increased likelihood of a significant loss of in vivo reproductive cell characteristics.

III. SUMMARY OF THE INVENTION

Accordingly, a broad object of the invention can be to provide compositions or extracts obtained from Sea Buckthorn plants which can be combined with reproductive cells to reduce the loss of in vivo reproductive cell characteristics or reduce the loss of reproductive cell characteristics of newly harvested reproductive cells, or reduce the loss of function of reproductive cells in vitro.

A second broad object of the invention can be to provide compositions or extracts obtained from Sea Buckthorn plants which can be combined with one or more diluents into which reproductive cells are transferred to reduce the loss of in vivo reproductive cell characteristics, or reduce the loss of reproductive cell characteristics of newly harvested reproductive cells, or reduce the loss of function of reproductive cells in vitro.

A third broad object of the invention can be to provide compositions or extracts obtained from Sea Buckthorn plants which can be transferred to containers or vessels into which reproductive cells are subsequently transferred to reduce the loss of in vivo reproductive cell characteristics, or reduce the loss of reproductive cell characteristics of newly harvested reproductive cells, or reduce the loss of function of reproductive cells in vitro.

A fourth broad object of the invention can be to provide compositions or extracts obtained from Sea Buckthorn plants which can be combined with reproductive cells (or combined with reproductive cells contained in one or more diluents) prior to or during a period in which the reproductive cells are cooled in temperature (or stored at a the cooled temperature) to reduce the loss of in vivo reproductive cell characteristics, or reduce the loss of reproductive cell characteristics of newly harvested reproductive cells, or reduce the loss of function of reproductive cells during the period of cooling or storage at cooled temperature.

A fifth broad object of the invention can be to provide compositions or extracts obtained from Sea Buckthorn plants which can be combined with reproductive cells (or reproductive cells contained in diluents) prior to freezing of such reproductive cells to reduce the loss of in vivo reproductive cell characteristics, or reduce the loss of reproductive cell characteristics of newly harvested reproductive cells, or reduce the loss of function of reproductive cells during freezing or storage of frozen reproductive cells.

A sixth broad object of the invention can be to provide compositions or extracts obtained from Sea Buckthorn plants which can be combined with sperm cells (or sperm cells contained in diluents) to generally reduce the loss of motility of such sperm cells, or reduce the loss of motility of such sperm cells due to conventional in vitro procedures, or reduce the loss of motility of such sperm cells due to a reduction or cooling of temperature, or reduce the loss of motility of such sperm cells due to freezing or due to frozen storage, or reduce the loss of motility of such sperm cells due to thawing of or thawed storage.

A seventh broad object of the invention can be to provide compositions or extracts obtained from Sea Buckthorn plants which can be combined with sperm cells (or sperm cells contained in diluents) to generally reduce the loss of fertility of such sperm cells, or reduce the loss of fertility of such sperm cells due to conventional in vitro procedures, or reduce the loss of fertility of such sperm cells due to a reduction or cooling of temperature, or reduce the loss of fertility of such sperm cells due to freezing or due to frozen storage, or reduce the loss of fertility of such sperm cells due to thawing of or thawed storage.

An eighth broad object of the invention can be to provide methods of combining one or more compositions or extracts obtained from Sea Buckthorn plants with reproductive cells and in particular provide methods of combining compositions or extracts obtained from Sea Buckthorn which are otherwise immiscible in reproductive cells (or reproductive cells in biological fluids or diluents) which are effective in reducing loss of function of reproductive cells, or in reducing loss of in vivo characteristics of reproductive cells, or in reducing the loss of function of reproductive cells in vitro A ninth broad object of the invention can be to provide one or more treated reproductive cell products obtained from the process of combining one or more compositions or extracts of Sea Buckthorn with reproductive cells.

Naturally, further objects of the invention are disclosed throughout other areas of the specification, drawings, photographs, and claims.

IV. A BRIEF DESCRIPTION OF THE DRAWINGS

FIG. 1 is a diagram which illustrates the process of obtaining compositions or extracts from plants of the genus *Hippophae*.

V. DETAILED DESCRIPTION OF THE PREFERRED EMBODIMENTS

Compositions or extracts obtained from plants of the genus *Hippophae* and methods of using such compositions to reduce loss of reproductive cell function.

DEFINITIONS

The term "*Hippophae*" refers to the genus of plants which, without limiting the plant members of the genus, includes the species *rhamnoides, salicifolia, tibetana, gvantsensis* and *neurocarpa* and plants identified by the common names Sea Buckthorn, Sandorn, Espino Falso, Oblebicha, Olivella Spinosa, Sallow Thorn, or Duindoorn.

The term "extract or extracts" refers to any moiety or moieties isolated from a plant; a portion of a plant such as the leaves, fruit, or seeds; or a plant product of *Hippophae* as above-described regardless as to whether such moiety or moieties are isolated singularly, or in multiple simultaneous fashion, or is a product of combining such moiety or moieties, or produced by molecular biology techniques or chemical synthesis techniques, and specifically includes, without limiting the forgoing, Extracts 1-9, as described below, any combination of such Extracts or any compound isolated from such Extracts.

The term "reproductive cell" refers to one or a plurality of oocytes, sperm cells, embryos, embryonic stem cells, or any other cells or cell lines, obtained from any species of animal useful for reproductive purposes including without limitation artificial insemination, in vitro fertilization, intra cytoplasmic sperm injection, or cloning and without limiting the forgoing encompasses bovine, equine, ovine, porcine, or avian sperm cells.

The term "diluent" refers to any solution that comes in contact with a reproductive cell such as buffered solutions which contain one or more of sodium citrate, Tris[hydroxymethyl]aminomethane, TES (N-Tris[Hydroxymethyl]methyl-2-aminoethanesulfonic acid), monosodium glutamate, HEPES; medium such as HEPES buffered medium, HEPES buffered bovine gamete medium and particularly HBGM3 as described by J. J. Parish "Capacitation of Bovine Sperm By Heparin" 38 Biology of Reproduction 1171 (1988); cell culture media; extenders such as E-Z Mixin, E-Z Freezin-MFR5 or E-Z Freezin-LE (Animal Reproduction Systems, 14395 Ramona Avenue, Chino, Calif.); and which can further contain cryoprotectants such as glycerol, dimethyl sulfoxide, ethylene glycol, propylene glycol; other organic substances such as egg yolk, an egg yolk extract, milk, a milk extract, casein, albumin, lecithin, bovine serum albumin, cholesterol; sugars such as the monosacharides, glucose, fructose, or mannose; detergents such as sodium dodecyl sulfate; antioxidants such butylated hydroxytoluene; capacitation facilitators such as alpha amylase, beta amylase, or beta glucuronidase; antibiotics such as tylosin, gentamicin, lincomycin, spectinomycin, linco-spectin (a combination of lincomycin and spectinomycin), penicillin, streptomycin, and ticarcillin; flow cytometer sheath fluids such as 98.6 mM sodium citrate dihydrate or 197 mM Tris(hydroxymethyl) aminomethane, 55.4 mM citric acid monohydrate and 47.5 mM fructose each adjusted to pH 6.8, which may be utilized for any purpose such as washing, culturing, handling, or cryopreserving the reproductive cell.

For purposes of the present invention, "embryo" refers to the stages of development whereby a conceptus develops into a fetus.

For purposes of the present invention, "embryonic stem cell" (ESC) refers to established cultured cell lines originating from a single embryo, each ESC population of cells having identical genetic material.

The term "combination or combining" refers to any method of putting two or more materials together. Such methods include, but are not limited to, mixing, blending, commingling, concocting, homogenizing, incorporating, intermingling, fusing, joining, shuffling, stirring, coalescing, integrating, confounding, joining, uniting, or the like.

The term "reduces loss of function" or "reducing the loss of function" refers to inhibiting events or decreasing the likelihood of events in vitro which damage, impair, diminish, or decrease the in vivo cellular characteristics of a reproductive cell such as events which: increase reproductive cell death, decrease reproductive cell fertility, decrease reproductive cell viability, decrease sperm motility, increase premature acrosome reactions, damage the lipid bilayer, damage cellular organelles, initiate or result in apoptosis, initiate or result in necrotic cells, generate reactive oxygen species (ROS), react reactive oxygen species with the reproductive cell, or the like, thereby, the in vivo cellular characteristics, or the cellular characteristics of newly collected or harvested reproductive cells, may be retained or retained to a greater degree in vitro as assessed by one or more assays when treated with extracts as compared to control reproductive cells (not treated with extracts), and can maintain such a state over an extended period of time. Measures of "in vivo cellular characteristics" may include, for example, motility, capacitation, cell leakage, DNA fragmentation, necrosis, or apoptosis.

The term "emulsifier" refers to a substance having the capacity to maintain a dispersion or suspension of two immiscible substances such as oil in water, and specifically includes, without limitation, egg yolk, orvus paste, lecithin, cyclodextrin, or the like.

For the purposes of the present invention, ranges may be expressed herein as from "about" one particular value to "about" another particular value. When such a range is expressed, another embodiment includes from the one particular value to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

Moreover, for the purposes of the present invention, the term "a" or "an" entity refers to one or more of that entity; for example, "a protein" or "an peptide" refers to one or more of those compounds or at least one compound. As such, the terms "a" or "an", "one or more" and "at least one" can be used interchangeably herein. Furthermore, a compound "selected from the group consisting of" refers to one or more of the compounds in the list that follows, including combinations of two or more of the compounds. According to the present invention, an isolated or biologically pure bioactive agent is a compound that has been removed from its natural milieu. As such, "isolated" and "biologically pure" do not necessarily reflect the extent to which the compound has been purified. An isolated compound of the present invention can be obtained from its natural source, can be produced using molecular biology techniques or can be produced by chemical synthesis.

Preparation of Extracts. Now referring primarily to FIG. 1, a variety of extracts can be obtained from plants encompassed by the genus *Hippophae* (1) useful in reducing the loss of function in reproductive cells. Pulp oil extract (including the non-limiting example of Extract 1) (2) can be prepared from the pulp and skin (3) of the fruit (or berries) (4) obtained from one or more species of *Hippophae* (1). The fruit (4) can be broken up, cut in pieces, or otherwise reduced as necessary (hereinafter "comminuted")(16) to allow separation of the juice (6) and whole seeds (9) from the fruit (4). Typically, the comminuted fruit (4) is pressed (7) to obtain the juice (6) and a press cake (8) of the pulp and skins (3) (and other solids which may be carried with the pulp and skins) and whole seeds (9). The whole seeds (9) can be separated from the pulp and skins (3). The pulp and skins (3) can be mixed and milled (10) and extracted (11) with hypercritical carbon dioxide (or with other solvents such as hexane) to obtain a pulp oil (including the non-limiting example of Extract 1)(2). Alternately, pulp oil (2) of *Hippophae* suitable for use as pulp oil extract (2) in the invention can be obtained from Leinig Wildfrucht-Verrarbeitung, Markische Str./Gewerbegebiet, DE-15806 Dabendorf, Germany.

The whole seeds (9) obtained in the above-described method for producing pulp oil extract (2) can be cleaned (12), ground (13) and extracted (14) with hypercritical carbon dioxide (or extracted with other solvents such as hexane) to generate seed oil extract (including the non-limiting example of Extract 2)(15). Alternately, seed oil (15) of *Hippophae* suitable for use in the invention can be obtained from Leinig Wildfrucht-Verrarbeitung, Markische Str./Gewerbegebiet, DE-15806 Dabendorf, Germany.

A carotenoid-lipoprotein complex extract (including the non-limiting example of Extract 5) (16) can also be derived from the pulp and skin solids (3) of the *Hippophae* fruit and obtained commercially from SC Proplanta, S.A., Str. Seslului 2, 400372, Cluj-Napoca, Romania.

A fruit tincture extract (including the non-limiting example of Extract 6) (17) can further be obtained by centrifugation (18) of the pulp and skins (3) at about 200 rounds per minute (rpm) to generate a lipoproteic fraction (LPF) (19). About five grams of the lipoproteic fraction (LPF) can be combined with about 200 mL of a 1:1 solution of 98 percent (%) ethanol (EtOH):distilled water (20). The mixture can be then be incubated (21) in the dark for five days at about 25 degrees centigrade (° C.). The use of particular numbers of particles, amounts, volumes, weights, or other measures throughout this description is not intended to limit the scalability of the invention, but rather to provide non-limiting examples of how to make and use particular embodiments of the invention. The mixture can then be filtered (22) to generate an amount of the fruit tincture extract (including the non-limiting example of Extract 6) (23). Alternately, a fruit tincture extract of *Hippophae* fruit suitable for use in the invention can be obtained from SC Proplanta, S.A., Str. Seslului 2, 400372, Cluj-Napoca, Romania.

Again referring to FIG. 1, a juice extract (including the non-limiting example of Extract 3) (24) of one or more species of *Hippophae* fruit or berries (4) suitable for use in the invention can be prepared by removing the vegetal portion and other debris from the fruit (4). The fruit (4) can be comminuted (16) sufficiently to allow the removal of the whole seeds (25) from the remaining fruit solids (26). The remaining fruit solids (26) can then be combined with about three volumes of ice cold phosphate buffered saline pH 7.4 (27). The resulting combination can be homogenized at about 0° C. until a homogeneous mixture (28) is obtained. The homogeneous mixture (28) can be transferred to a centrifuge container and centrifuged (29) at 2500×g at about 4° C. for about 10 minutes (min). The supernatant (including the non-limiting example of Extract 3) (24) can be utilized directly in embodiments of the invention or can be stored at about −70° C. The centrifugation pellet obtained as above-described containing pulp and skin solids (along with other solids carried with the pulp and skin solids) can be utilized in various embodiments of the invention as berry sediment extract (including the non-limiting example of Extract 4) (25). Alternately, a juice extract of *Hippophae* fruit suitable for use in the invention can be obtained from Seabuckthorn International Inc., 4154 Ponderosa Drive, Peachland, BC V0H1X5.

The leaves of plants of the genus *Hippophae* ("leaves")(26) can be separated from the stems and other debris. Fifty grams of the leaves (26) can be comminuted (27) and combined with 500 mL of a 1:2 solution of 98% EtOH:distilled water (28).

The mixture can be incubated (29) in the dark for five days at about 25° C. The mixture can be filtered (30) to provide a leaf tincture (including the non-limiting example of Extract 7) (31). Alternately, a leaf tincture extract suitable for use in the invention can be obtained from SC Proplanta, S.A., Str. Seslului 2, 400372, Cluj-Napoca, Romania.

Similarly, fifty grams of the leaves (26) can be comminuted (27) then combined with 670 mL paraffin oil (32). The mixture can be heated (33) for 5 min and incubated (34) in the dark for a period of about five days at about 25° C. The mixture can be filtered (35) to provide a leaf paraffin oil (including the non-limiting example of Extract 8) (36). Alternately, a suitable leaf paraffin oil extract (36) suitable for use in the invention can be obtained from SC Proplanta, S.A., Str. Seslului 2, 400372, Cluj-Napoca, Romania.

Again, fifty grams of the leaves (26) can be comminuted (27) then combined with about 500 mL 1:1 glycerol:distilled water (37). The mixture can be heated (38) for 5 min and incubated (39) in the dark for a period of about five days at about 25° C. The mixture can be filtered (40) to provide a leaf hydroglycerin extract (including the non-limiting example of Extract 9)(41). Alternately, a suitable leaf hydroglycerin extract (41) for use in the invention can be obtained from SC Proplanta, S.A., Str. Seslului 2, 400372, Cluj-Napoca, Romania.

General Use Of Extracts. In general the invention encompasses combining an amount of one or more extracts with reproductive cells directly or indirectly sufficient to reduce loss of function of in vivo reproductive cell characteristics. Extract(s) can be combined directly with reproductive cells contained in an amount of biological fluid, such as sperm cells contained in an amount of seminal fluid, and which may thereafter be combined with an amount of one or more diluents in a single or a plurality of steps. Alternately, reproductive cells can be combined with one or more diluents and an amount of extract added to the combination of reproductive cells and diluents. Additionally, an amount of one or more extracts can be transferred to a container or vessel to which diluents or reproductive cells are thereafter transferred. The extracts may in certain instances be transferred to the container or vessel and an amount of the solvent in the extract removed to allow the extract to adhere to the container or vessel wall surface. Additionally, extracts can be utilized in vivo to condition the reproductive tract for artificial insemination or natural insemination, in vivo fertilization of oocytes, embryo implantation, or the like. As to these embodiments of the invention, the extracts can be administered vaginally in the form of inserts, gels, foams, pessaries, suppositories, or the like. In an alternative or complimentary embodiment, extracts may be administered as a cream or gel on the male genitalia. Compositions for vaginal administration may contain gelatinizing agents, lubricating agents or other additives compatible with extracts and the reproductive environment. Extracts can also be utilized on resulting zygotes or embryos during in vitro development or prior to intrauterine transfer. Particular embodiments of the invention include the combination of an effective amount of one or more extracts into any conventional method in which reproductive cells are used. While specific examples of combining reproductive cells with one or more extracts have been described, these particular examples are not intended to be limiting but rather illustrative of the numerous and varied methods by which an effective amount of one or more extracts can be combined with an at least one or a plurality of reproductive cells to reduce loss of function of in vivo characteristics.

Collection of Reproductive Cells. As to particular embodiments of the invention, extracts (including without limitation Extracts 1-9) described below, can be combined with collected reproductive cells from a female or a male donor animal. Specifically, with respect to semen collected from cattle or horses via artificial vagina, or manual or electrical manipulation of the penis, extracts can be combined directly with the seminal plasma of the freshly collected semen or indirectly by combination of the extract with a diluent which can then be combined with the collected semen. An effective amount of the extract can also be combined with sperm cells in which the seminal plasma is lacking or has been removed (whether to the sperm cells directly, after being combined with a diluent, or to the diluent then combined with such sperm cells). The effective amount of extract combined with the sperm cells can vary and be adjusted dependant upon the application, species, volume of ejaculate, or like parameters.

In another embodiment of the present invention, extracts can be combined with the diluent into which freshly harvested eggs are transferred. Alternately, freshly harvested eggs can be transferred to the diluent in a petri dish or other container and then one or more extracts thereafter combined with the diluent in the petri dish, or other container into which the egg(s) have been transferred. Similarly, an effective amount of one or more extracts can be added as an ingredient to the media in which oocytes are bathed upon collection.

Processing of Reproductive Cells. In another particular embodiment of the invention, extracts can be utilized to reduce loss of function of reproductive cells during the various steps of a process preparing the reproductive cells for use. An amount of one or more extracts can be combined with the reproductive cells in one or more steps of the process in sufficient amount to reduce the loss of function, or otherwise mitigate damage to the reproductive cell, without compromising the integrity of the solution(s) used in the modified procedural step.

Specifically in regard to processing sperm cells, multi-step processing steps often cause significant damage to sperm, especially in the cases of multi-step processes like flow analysis or flow sorting of sperm cells used to obtain sex selected inseminates used for inseminations to achieve offspring of a specified, or pre-selected sex. During sperm cell sexing processes sperm cells can be exposed to reactive oxygen species (ROS), and extracts can be useful in reducing loss of function of the sperm cells by combination with the initial ejaculate, to extended sperm cells, the sheath fluid used during the analysis and sorting process, to the DNA staining solution, to the collection fluid, to the sperm post-sort and post-centrifugation, in the diluents used for freezing the sperm, or in the vessel used for freezing sperm cells. Extracts utilized in such key steps can substantially reduce the loss of motility of the sex selected inseminates at the time of artificial insemination and can increase the likelihood of pregnancy of the female recipient.

In another embodiment of the invention, an effective amount of one or more extracts can be combined to previously disclosed sperm cell extenders or diluents. The amount of extract combined or the concentration of extract in the extender or diluent achieved can be adjusted to provide an effective amount of extract depending on the species or subspecies from which the reproductive cells are derived, or the individual animal from which the reproductive cells are collected. Extracts can be combined with the extender or diluent in concentrations ranging from nanogram concentrations to milligram concentrations. Such addition, can occur as the extender or diluent is being made, or just prior to use.

Examples of such solutions include egg yolk TALP, skim or whole milk extender, or the like.

In another embodiment of the invention, extracts can be adhered to beads used for separation of sperm cells during centrifugation, gravity sedimentation, or column elution to prevent oxidation during events which expose sperm cells to oxygen. Specific examples include Percoll gradients commonly used to isolate spermatozoa from seminal plasma. Extracts could be attached to Percoll, or similar beads using knowledge commonly known in the art.

In another embodiment of the invention, extracts can be combined to the media used over a centrifugation gradient, or column, to help limit the amount of oxidants in the solution and thus limit sperm cell exposure to oxidants. Examples of such media include Biggers, Whitten and Whittingham (BWW), and Earle's media.

In yet another embodiment of the invention, extracts can be combined with diluents or culture media utilized to incubate oocytes until they mature and can be utilized in diluents or media utilized during fertilization or for freezing. Such culture media include Irvine's media or the like. Extracts can be combined in concentrations sufficient to reduce external ROS, and reduce oxidized lipids in the oocyte membrane, and reduce damage from damaging compounds in the environment, yet low enough to avoid affecting the pH and osmotic potential of the solution.

Cooling or Freezing of Reproductive Cells. In a particular embodiment of the present invention, extracts can be utilized to reduce loss of function of reproductive cells during the steps of cooling or freezing of diluents for reproductive cell storage and during the steps of warming the diluents for subsequent use of the reproductive cells in various applications. During extended storage, gamete membranes are can be most susceptible to damage by free radicals, internally or externally generated, ice crystals, bacterial damage, and damage from other substances in the diluents.

The assessment of sperm cell motility can provide a model for assessing the effectiveness of extracts obtained from plants of the genus *Hippophae* to reduce loss of function of reproductive cells, to reduce the loss of in vivo characteristics of reproductive cells, to reduce the loss of in vivo characteristics of newly harvested reproductive cells, and specifically, to reduce the loss of fertility of sperm cells. As to each, the assessment of sperm cell motility can be less costly, less difficult, and less time consuming, than assessment of the effectiveness of extracts based on other measures of reproductive cells such as assessment of membrane damage. Recently, Kirk, et al. "Comparison of In Vitro Laboratory Analyses with the Fertility of Cryopreserved Stallion Spermatozoa", Theriogenology 64: 1422-1439 (2005) studied the correlation of several inexpensive, rapid assays to the fertility of stallion sperm cells. The best one-variable model for predicting fertility was the percentage motile sperm cells at about 90 minutes post-thaw ($r^2$=0.60)("90 minute motility"). Interestingly, the best two, and three variable models also included 90 minute motility. The best four variable model included 90 minute motility, as well as 0 minute motility, percentage of live sperm cells and the percentage of live-acrosome intact sperm cells ($r^2$=0.79). Therefore, assessing the effectiveness of extracts of *Hippophae* to reduce loss of motility in sperm cells using a 90 minute motility post-thaw assessment, or two hours post-warm motility assessment, can provide a measure of the effectiveness of extracts of plants in the genus *Hippophae* to reduce loss of function of sperm cells, or the loss of fertility of sperm cells, or both, which may be useful in assessing the effectiveness of *Hippophae* extracts in reducing the loss of function of other types of reproductive cells.

EXAMPLE 1

In a first experiment (data set out to the right of Exp 1 in Tables 1-6), semen was collected from two stallions via artificial vagina. The motility of each ejaculate was determined subjectively via light microscope and the semen was diluted to a final concentration of about $5 \times 10^8$ motile sperm cells/ml with E-Z freezin LE (Animal Reproduction Systems, Chino, Calif.) and combined to one each of thirteen 0.25 mL semen samples was an amount of a corresponding one of thirteen adjuvants: (1) no addition-control ("untreated control semen sample); 2) about 5% cyclodextrin; 3) about 2.5% cyclodextrin; 4) about 5% pulp oil in cyclodextrin; 5) about 2.5% pulp oil in cyclodextrin; 6) about 5% seed oil in cyclodextrin; 7) about 2.5% seed oil in cyclodextrin; 8) emulsion of about 5% seed oil, 9) emulsion of about 2.5% seed oil, 10) emulsion of about 5% pulp oil, 11) emulsion of about 2.5% pulp oil, 12) about 5% juice, and 13) about 2.5% juice. Throughout this description the amount of extract is expressed as a percentage volume to volume (v/v) unless otherwise indicated.

Following dilution of each semen sample with E-Z freezin LE and combining the diluted semen with the corresponding adjuvant ("treated semen samples"), the treated semen samples were cooled by reducing the temperature at a controlled rate to about 5° C. Treated semen samples were then frozen by conventional procedures on racks in static liquid nitrogen vapor.

Frozen treated semen samples were subsequently thawed in a water bath at about 37° C. and estimates of motility were made after incubating samples at about 37° C. for 0 and 2 hours (h) post-thawing. Cyclodextrin proved to be spermicidal in this study, and therefore motility data is not shown for those treatments that contain cyclodextrin alone or in combination with the oils.

Now referring to Tables 1-6 below, the results show that in general the treated semen samples containing adjuvants with pulp oil extract, seed oil extract, or juice extract at either 2.5% or 5% v/v (Extracts 1, 2, or 3 (2)(15)(24) at either 2.5% or 5% v/v) exhibited a reduced loss of motility as compared with the untreated control semen sample.

EXAMPLE 2

In a second experiment (data set out to the right of Exp 2 in Tables 5-6), semen was collected from one stallion via artificial vagina. The motility of the ejaculate was determined objectively using a Hamilton-Thorn sperm analyzer with a 37° C. stage warmer. The assessed data included percentage of motile sperm cells, progressive motile sperm cells, as well as average path velocity, straight line velocity, and straightness of motile sperm cells in accordance with conventional operating procedures for the instrument. The semen was diluted to a final concentration of about $5 \times 10^8$ motile cells/ml with E-Z Mixin CST (Animal Reproduction Systems, Chino, Calif.) and to each of fifteen aliquots of 0.25 mL one each of fifteen adjuvants was combined: (1) no addition-control, 2) about 5% cyclodextrin control, 3) about 2.5% cyclodextrin, 4) about 5% pulp oil in cyclodextrin, 5) ab about 2.5% pulp oil in cyclodextrin, 6) about 5% seed oil in cyclodextrin, 7) about 2.5% seed oil in cyclodextrin, 8) emulsion of about 5% seed oil, 9) emulsion of about 2.5% seed oil, 10) emulsion of about 5% pulp oil, 11) emulsion of about 2.5% pulp oil, 12) about 5% juice, 13) about 2.5% juice 14) about 5% berry sediment, and 15) about 2.5% berry sediment.

Following dilution of each semen sample with E-Z Mixin CST and the corresponding adjuvant, the treated semen samples were cooled by reducing the temperature at a controlled rate to about 4° C. Motility was evaluated subjectively via light microscope immediately at 24, 38, and 72 h after being held at about 4° C. Motility of each treated semen sample was examined again after 2 h at about 37° C.

Cyclodextrin again proved to be spermicidal in this study, and therefore motility data is not shown for those treatments. In addition the berry sediment was spermicidal (likely due to pH related issues, not issues inherent to the berry sediment), and therefore motility data is not shown.

Now referring to Tables 5 and 6, the results show that the treated semen samples containing adjuvants with juice extract at either 2.5% or 5% v/v (Extract 3 (24) at either 2.5% or 5% v/v) exhibited a reduced loss of motility of sperm cells as compared with the untreated control semen sample.

EXAMPLE 3

In a third experiment (data set out to the right of Exp 2 in Tables 1-6) Semen was collected from one stallion via artificial vagina. The motility of the ejaculate was determined subjectively via light microscope prior to cooling. The semen was diluted to a final concentration of about $6 \times 10^8$ motile cells/ml with E-Z Freezin LE (Animal Reproduction Systems, Chino, Calif.) containing about 20% egg yolk and about 0.1% orvus paste plus and each of seven 0.25 mL aliquots was combined with a corresponding one each of adjuvant as follows: (1) no addition-control, 2) emulsion of about 5% seed oil, 3) emulsion of about 2.5% seed oil, 4) emulsion of about 5% pulp oil, 5) emulsion of about 2.5% pulp oil, 6) about 5% juice, and 7) about 2.5% juice.

Following dilution of each semen sample with E-Z Freezin LE plus the corresponding adjuvant (treated semen samples), the treated semen samples were cooled by reducing the temperature at a controlled rate to about 4° C. Motility was evaluated subjectively via light microscope immediately at about 24, 48, and 72 h post-cooling using the Hamilton-Thorn sperm analyzer five minutes after warming to about 37° C. and again after being held for about 2 hr at about 37° C.

Now referring to Tables 1-6 below, the results show that in general the treated semen samples containing adjuvents with pulp oil extract, seed oil extract, or juice extract at either 2.5% or 5% v/v (Extracts 1, 2, or 3 (2)(15)(24) at either 2.5% or 5% v/v) exhibited a reduced loss of motility as compared with the untreated control semen sample.

EXAMPLE 4

In a fourth through seventh experiment (the data set out to the right of Exp 4, Exp 5, Exp 6 & Exp 7 in Tables 1-14), semen was collected from two stallions (experiments 6 & 7; one stallion experiments 4 & 5) via artificial vagina. The motility of each ejaculate was determined objectively using a Hamilton-Thorn Sperm Analyzer prior to cooling. The semen was diluted to a final concentration of about $6 \times 10^8$ motile cells/ml with E-Z Mixin CST (Animal Reproduction Systems, Chino, Calif.) containing about 20% egg yolk and about 0.1% orvus paste and to each of 15 0.25 mL aliquots was combined one adjuvant as follows: (1) no addition-control; 2) about 5% pulp oil; 3) about 2.5% pulp oil; 4) about 5% seed oil; 5) about 2.5% seed oil; 6) about 5% juice; 7) about 2.5% juice; 8) about 5% fruit alcohol extract; 9) about 2.5% fruit alcohol extract; 10) about 5% leaf alcohol extract; 11) about 2.5% leaf alcohol extract; 12) about 5% leaf glycerine extract; 13) about 2.5% leaf glycerine extract; 14) about 5% leaf paraffin; or 15) about 2.5% leaf paraffin.

Following dilution of each semen sample with E-Z Mixin CST and containing the corresponding adjuvant (treated semen samples), the treated semen samples were cooled by reducing the temperature at a controlled rate to about 4° C. Motility was evaluated objectively using a Hamilton-Thorn Sperm Analyzer at about 24, 48 and 72 hours after cooling. Motility was evaluated after being warmed for about 5 minutes to about 37° C., and again after being held for about 120 minutes at about 37° C. For each evaluation a minimum of 500 sperm per treatment were analyzed. For experiment 6 and 7, motility data from two stallions is averaged for each treatment, and each time point.

Now referring to Tables 1-14 below, the results show that embodiments of the invention which combine pulp oil extract (2), seed oil extract (15), juice extract (24), fruit tincture extract (23), leaf tincture extract (31), leaf paraffin extract (36), or leaf hydroglycerin extract (41) (and in particular embodiments of the invention which combine Extracts 1-3 and 6-9) with reproductive cells (and in particular sperm cells) can reduce loss of function (and in particular the loss of post warming motility in sperm cells at about 24, 48 and 72 hours after cooling), when compared to the control samples. With respect to sperm cells, the reduced loss of motility associated with the use of extracts can even be more pronounced after sperm cells are held for 2 hours. While there can be variability with respect to the reduced loss of motility in response to the use of extracts both between stallions as well as within ejaculates from the same stallion, the juice extract (24), leaf tincture extract (31), and fruit tincture extract (23) consistently reduce loss of motility at and between both time points (see Tables 5-8 and 13-14 column labeled 'difference 2 hr-2 hr control for a reflection of the difference in motility for the extract treated sperm cells versus the control sperm cells). Only 2.5% leaf paraffin extract (36) (but effective at 5% leaf paraffin extract) does not appear to be effective by itself, for cooled sperm cells but might be effective in combination with other extracts, or for frozen sperm cells. Additionally, the average speed of the motile sperm cells treated with Extracts 1-3 and 6-9 can be increased as compared to the untreated control sperm cell samples, both immediately after warming to about 37° C., and after about 2 hours at room temperature.

EXAMPLE 5

The antioxidant potential of Extracts 1-3 and 6-9 was analyzed using a kit by Oxford Biomedical Research, P.O. Box 522, Oxford Mich. 48371. This colorimetric microplate assay allows comparison of each Extract 1-3 and 6-9 to a standard to determine the total copper reducing equivalents. Generally the assay was performed by preparing the standards, and allowing dilution buffer, copper solution and stop solution to equilibrate to room temperature for about 30 minutes prior to running the assay. Both Extracts 1-3 and 6-9 samples and standards were diluted 1:40 in the provided dilution buffer (e.g. 15 mL serum+585 mL buffer). Next, 200 mL of diluted Extract samples or standards were placed in each well. The plate was read at 490 nanometers (nm) for a reference measurement, Then 50 mL of Cu++ solution was added to each well and incubated about 3 minutes at room temperature. 50 mL of stop solution was added and the plate read a second time at 490 nm.

The data in Table 15 demonstrates the antioxidant potential of each of Extracts 1-3 and 6-9 at two different concentrations. The data further explains the effectiveness of extracts against damaging oxidant or ROS events (above discussed) generated during in vitro processing of reproductive cells.

TABLE 1

2.5% Pulp oil (2)

| | treated | | control | | |
|---|---|---|---|---|---|
| | 0 hr motility | 2 hr @ 37 C. | 0 hr motility | 2 hr @ 37 C. | difference |
| Exp 1- frozen | 40 | 22 | 32 | 15 | 7 |
| | 72 hr motility | 2 hr @ 37 C. | 72 hr motility | 2 hr @ 37 C. | |
| Exp 3-cooled | 40 | 35 | 60 | 23 | 12 |
| Exp 4-cooled | 39 | 36 | 42 | 18 | 18 |
| Exp 5-cooled | 54 | 10 | 33 | 21 | −11 |
| Exp 6 cooled | 39 | 36 | 42 | 18 | 18 |
| Exp 7 cooled | 56 | 10 | 34 | 21 | −11 |

TABLE 2

5% Pulp Oil (2)

| | treated | | control | | |
|---|---|---|---|---|---|
| | 0 hr motility | 2 hr @ 37 C. | 0 hr motility | 2 hr @ 37 C. | difference |
| Exp 1- frozen | 46 | 28 | 32 | 15 | 13 |
| | 72 hr motility | 2 hr @ 37 C. | 72 hr motility | 2 hr @ 37 C. | |
| Exp 3-cooled | 42 | 15 | 60 | 23 | −8 |
| Exp 4-cooled | 21 | 24 | 42 | 18 | 6 |
| Exp 5-cooled | 40 | 21 | 33 | 21 | 0 |
| Exp 6 cooled | 21 | 24 | 42 | 18 | 6 |
| Exp 7 cooled | 40 | 21 | 34 | 21 | 0 |

TABLE 3

2.5% Seed Oil (15)

| | treated | | control | | |
|---|---|---|---|---|---|
| | 0 hr motility | 2 hr @ 37 C. | 0 hr motility | 2 hr @ 37 C. | difference |
| Exp 1- frozen | 45 | 35 | 32 | 15 | 20 |
| | 72 hr motility | 2 hr @ 37 C. | 72 hr motility | 2 hr @ 37 C. | |
| Exp 3- cooled | 36 | 36 | 60 | 23 | 13 |
| Exp 4-cooled | 52 | 38 | 42 | 18 | 20 |
| Exp 5-cooled | 52 | 12 | 33 | 21 | −9 |
| Exp 6 cooled | 51 | 38 | 42 | 18 | 20 |
| Exp 7 cooled | 52 | 22 | 34 | 21 | 1 |

TABLE 4

5% Seed Oil (15)

| | treated | | control | | |
|---|---|---|---|---|---|
| | 0 hr motility | 2 hr @ 37 C. | 0 hr motility | 2 hr @ 37 C. | difference |
| Exp 1- frozen | 48 | 30 | 32 | 15 | 15 |
| | 72 hr motility | 2 hr @ 37 C. | 72 hr motility | 2 hr @ 37 C. | |
| Exp 3-cooled | 43 | 18 | 60 | 23 | −5 |
| Exp 4-cooled | 22 | 19 | 42 | 18 | 1 |
| Exp 5-cooled | 48 | 23 | 33 | 21 | 2 |
| Exp 6 cooled | 24 | 19 | 42 | 18 | 1 |
| Exp 7 cooled | 47 | 43 | 34 | 21 | 22 |

TABLE 5

2.5% Juice (24)

| | treated | | control | | difference |
|---|---|---|---|---|---|
| | 0 hr motility | 2 hr @ 37 C. | 0 hr motility | 2 hr @ 37 C. | (2 hr − 2 hr control) |
| Exp 1- frozen | 41 | 28 | 32 | 15 | 13 |
| | 0 hr motility | 24 hours post cool | 0 hr motility | 24 hours post cool | |
| Exp 2-cooled | 77.5 | 55 | 67.5 | 52.5 | 2.5 |
| | 72 hr motility | 2 hr @ 37 C. | 72 hr motility | 2 hr @ 37 C. | |
| Exp 3-cooled | 58 | 28 | 60 | 23 | 5 |
| Exp 4-cooled | 43 | 28 | 42 | 18 | 10 |
| Exp 5-cooled | 63 | 22 | 33 | 21 | 1 |
| Exp 6 cooled | 51 | 38 | 42 | 18 | 20 |
| Exp 7 cooled | 65 | 24 | 34 | 21 | 3 |

TABLE 6

5% Juice (24)

| | treated | | control | | difference |
|---|---|---|---|---|---|
| | 0 hr motility | 2 hr @ 37 C. | 0 hr motility | 2 hr @ 37 C. | (2 hr − 2 hr control) |
| Exp 1- frozen | 39 | 5 | 32 | 15 | −10 |
| | 0 hr motility | 24 hours post cool | 0 hr motility | 24 hours post cool | |
| Exp 2-cooled | 80 | 67.5 | 67.5 | 52.5 | 15 |
| | 72 hr motility | 2 hr @ 37 C. | 72 hr motility | 2 hr @ 37 C. | |
| Exp 3-cooled | 60 | 56 | 60 | 23 | 33 |
| Exp 4 cooled | 58 | 38 | 42 | 18 | 20 |
| Exp 5-cooled | 62 | 26 | 33 | 21 | 5 |
| Exp 6 cooled | 57 | 39 | 42 | 18 | 21 |
| Exp 7 cooled | 64 | 26 | 34 | 21 | 5 |

TABLE 7

2.5% Fruit Tincture (23)

| | treated | | control | | |
|---|---|---|---|---|---|
| | 72 hr motility | 2 hr @ 37 C. | 72 hr motility | 2 hr @ 37 C. | |
| Exp 4-cooled | 58 | 33 | 42 | 18 | 15 |
| Exp 5-cooled | 63 | 42 | 33 | 21 | 21 |
| Exp 6 cooled | 58 | 33 | 42 | 18 | 15 |
| Exp 7 cooled | 64 | 43 | 34 | 21 | 22 |

TABLE 8

5% Fruit Tincture (23)

|  | treated | | control | | |
| --- | --- | --- | --- | --- | --- |
|  | 72 hr motility | 2 hr @ 37 C. | 72 hr motility | 2 hr @ 37 C. | |
| Exp 4-cooled | 52 | 30 | 42 | 18 | 12 |
| Exp 5-cooled | 65 | 21 | 33 | 21 | 0 |
| Exp 6 cooled | 52 | 30 | 42 | 18 | 12 |
| Exp 7 cooled | 66 | 22 | 34 | 21 | 1 |

TABLE 9

2.5% Leaf Paraffin (36)

|  | treated | | control | | |
| --- | --- | --- | --- | --- | --- |
|  | 72 hr motility | 2 hr @ 37 C. | 72 hr motility | 2 hr @ 37 C. | |
| Exp 4 | 42 | 11 | 42 | 18 | −7 |
| Exp 5-cooled | 40 | 5 | 33 | 21 | −16 |
| Exp 6 cooled | 43 | 12 | 42 | 18 | −6 |
| Exp 7 cooled | 40 | 7 | 34 | 21 | −14 |

TABLE 10

5% Leaf Paraffin (36)

|  | treated | | control | | |
| --- | --- | --- | --- | --- | --- |
|  | 72 hr motility | 2 hr @ 37 C. | 72 hr motility | 2 hr @ 37 C. | |
| Exp 4 | 51 | 28 | 42 | 18 | 10 |
| Exp 5-cooled | 53 | 20 | 33 | 21 | −1 |
| Exp 6 cooled | 51 | 28 | 42 | 18 | 10 |
| Exp 7 cooled | 55 | 20 | 34 | 21 | −1 |

TABLE 11

2.5% Leaf Glycerine (41)

|  | treated | | control | | |
| --- | --- | --- | --- | --- | --- |
|  | 72 hr motility | 2 hr @ 37 C. | 72 hr motility | 2 hr @ 37 C. | |
| Exp 4-cooled | 61 | 19 | 42 | 18 | 1 |
| Exp 5-cooled | 55 | 21 | 33 | 21 | 0 |
| Exp 6 cooled | 62 | 18 | 42 | 18 | 0 |
| Exp 7 cooled | 52 | 12 | 34 | 21 | −9 |

TABLE 12

5% Leaf Glycerine (41)

|  | treated | | control | | |
| --- | --- | --- | --- | --- | --- |
|  | 72 hr motility | 2 hr @ 37 C. | 72 hr motility | 2 hr @ 37 C. | |
| Exp 4-cooled | 68 | 18 | 42 | 18 | 0 |
| Exp 5-cooled | 73 | 22 | 33 | 21 | 1 |
| Exp 6 cooled | 68 | 17 | 42 | 18 | −1 |
| Exp 7 cooled | 72 | 16 | 34 | 21 | −5 |

TABLE 13

2.5% Leaf Tincture (31)

|  | treated | | control | | |
| --- | --- | --- | --- | --- | --- |
|  | 72 hr motility | 2 hr @ 37 C. | 72 hr motility | 2 hr @ 37 C. | |
| Exp 4-cooled | 58 | 22 | 42 | 18 | 4 |
| Exp 5-cooled | 71 | 11 | 33 | 21 | −10 |
| Exp 6 cooled | 58 | 23 | 42 | 18 | 5 |
| Exp 7 cooled | 72 | 12 | 34 | 21 | −9 |

TABLE 14

5% Leaf Tincture (31)

|  | treated | | control | | |
| --- | --- | --- | --- | --- | --- |
|  | 72 hr motility | 2 hr @ 37 C. | 72 hr motility | 2 hr @ 37 C. | |
| Exp 4-cooled | 63 | 21 | 42 | 18 | 3 |
| Exp 5-cooled | 70 | 51 | 33 | 21 | 30 |
| Exp 6 cooled | 62 | 21 | 42 | 18 | 3 |
| Exp 7 cooled | 70 | 41 | 34 | 21 | 20 |

TABLE 15

| Extract | μM Copper reducing equivalents at 2.5% of Extract | μM Copper reducing equivalents at 5% of Extract |
| --- | --- | --- |
| Extract 1: pulp oil extract (2) | 330.5 | 1148.8 |
| Extract 2: Seed oil extract (15) | 149.5 | 967.8 |
| Extract 3: juice extract (24) | 1290.4 | 1377 |
| Extract 6: fruit tincture extract (23) | 653.1 | 613.7 |
| Extract 7: leaf tincture extract (31) | 1038.6 | 1565.8 |
| Extract 8: leaf paraffin extract (36) | 692.4 | 1219.6 |
| Extract 9: leaf hydroglycerine extract (41) | 1691.7 | 1479.3 |

Production of Embryos and Embryo Storage. The production of embryos via artificial means such as in vitro fertilization (IVF), intracytoplasmic sperm injection (ICSI), zona drilling, zona dissection, and subzonal insertion of sperm (SUZI), involves much manipulation and potential exposure to oxygen, ROS and other potentially negative compounds. A particular embodiment of the present invention comprises the combination or addition of extracts to the media, diluent, or to the tools and containers used during such manipulation.

In another embodiment of the invention, extracts can be combined or added to the solution used to buffer the gametes during micro-manipulation for such procedures as IVF, ICSI, GIFT, ZIFT and other procedures which utilize the in vitro addition of sperm cells to an oocyte. Alternatively, or in addition, extracts can be utilized to coat the interior surfaces of tools (e.g., petri dish, micromanipulating needles, and the like).

After the addition of sperm cells to the oocyte, the resulting embryo must be washed to remove excess seminal plasma and additional sperm cells. In another embodiment of the present invention, this washing step via centrifugation, gravity column, or simple washing could utilize extracts, in the diluents or solutions, or attached by various methods, to the media used for separation. Additionally, oocytes can be stored for approximately 24 hours post-fertilization. Extracts could be present in the incubating media or diluent in order to protect the rapidly dividing cell from internally or externally generated free radicals.

In another embodiment of the invention, extracts can be added to the solution utilized to preserve embryos via freezing. Such an addition would confer protection immediately, and post-thaw when membranes, negatively affected by freezing, would be susceptible to free radical attack.

In yet another embodiment of the present invention, extracts would be added to the solution utilized to flush embryos from superovulated, inseminated females. The collected embryos can then be washed using extract containing media or diluents, and transferred to diluents or solutions, which may contain extracts in various concentrations, for freezing. Alternatively, the collected embryos may be transferred directly to a recipient.

In still another embodiment of the present invention, the addition of extracts to the media would include, equipment or containers for embryos as they are manipulated for embryo splitting, embryo sexing or during production of clones from cell-banked tissue lines, or other tissue sources or production of ESCs. Such addition would confer protection during manipulation, during freezing, and during post-thaw implantation, and/or manipulation.

In another embodiment of the invention, extracts could be utilized in solution, on containers or equipment used to produce, or achieve cloned offspring, transgenic animals or similar embryo-manipulating technologies.

Reproductive Aids. In a particular embodiment of the present invention, extracts can be used to condition the in vivo reproductive tract for conception. Extracts would be added vaginally in the form of an insert, gel, foam, pessary or suppository. Such compositions may contain gelatinizing agents, lubricating agents and other additives compatible with Extracts and the reproductive environment. Vaginal administration may occur at a predetermined time prior to sexual intercourse or artificial insemination, or may occur immediately after sexual intercourse or artificial insemination. In an alternative or complimentary embodiment, Extracts may be administered as a cream or gel on the male genitalia prior to sexual intercourse. In yet another embodiment, extracts are administered directly to the uterine environment. The presence of extracts in the vaginal environment and/or uterus would decrease oxidative damage to reproductive cells, reduce inflammation and/or act as an antibiotic. In particular, the compositions and methods of the present invention will result in an increased number of sperm reaching the oocyte, thereby improving the odds of conceiving.

Extracts as an Additive. This invention is directed to the medium additive extracts described above, media containing extracts, a method of making the medium supplement, a method of making media containing extracts and kits containing the medium supplement.

Extracts can be added to any cell culture media, including but not limited to, a reproductive cell wash media, a reproductive cell culture media, a reproductive cell transfer media, a reproductive cell cryopreservation media, (to include both freezing and vitrification procedures), cell collection media and cell sorting, or sexing media. Any media that can support reproductive cell development can be used, which includes, bicarbonate buffered medium, Hepes-buffered or MOPES buffered medium, phosphate buffered saline and the like.

Extracts may be prepared as a separate media supplement that is added to the media after media preparation, or it can be added directly to the media during media preparation. By way of example, extracts may be prepared on its own as follows. Extracts may be made into a stock solution by adding water, saline or media to make a concentrated stock solution. Alternatively, the solution may be obtained as a stock solution. Alternatively, extracts can be added directly to the media as either a powder or stock solution.

Extracts may also be adhered to a container or equipment useful for producing, manipulating, culturing or processing reproductive cells. In a particular embodiment, Extracts may be adhered to beads useful for separation of reproductive cells via centrifugation, gravity sedimentation, column elution and the like. In another particular embodiment, Extracts may adhere to a container via antibodies, proteins and the like. In yet another particular embodiment, extracts are applied to a container to create a liquid coating of such container. In yet another particular embodiment, Extracts is applied to a container as part of a solid coating or film which dissolves or otherwise releases Extracts upon contact with liquid media.

As can be easily understood from the foregoing, the basic concepts of the present invention may be embodied in a variety of ways. The invention involves numerous and varied compositions or extracts obtained from plants of the genus *Hippophae* and methods of using such compositions or extracts to reduce loss of reproductive cell function.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "diluent" should be understood to encompass disclosure of the act of "diluting"—whether explicitly discussed or not—and, conversely, were there effectively disclosure of the act of "diluting", such a disclosure should be understood to encompass disclosure of a "diluent" and even a "means for diluting." Such alternative terms for each element or step are to be understood to be explicitly included in the description.

In addition, as to each term used it should be understood that unless its utilization in this application is inconsistent with such interpretation, common dictionary definitions should be understood to included in the description for each term as contained in the Random House Webster's Unabridged Dictionary, second edition, each definition hereby incorporated by reference.

Thus, the applicant(s) should be understood to claim at least: i) each of the compositions or extracts herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

The claims set forth below are intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

The invention claimed is:

1. A method of reducing loss of function of reproductive cells, comprising the steps of:
    a. generating an extract of *Hippophae*;
    b. obtaining said reproductive cells of an animal; and
    c. combining said reproductive cells of said animal with an amount of said extract of *Hippophae* effective upon contact with said reproductive cells to reduce loss of function.

2. The method of reducing loss of function of reproductive cells according to claim 1, wherein said extract of *Hippophae* is selected from the group including: a seed extract, a seed oil extract, a pulp oil extract, a fruit extract, a fruit tincture extract, a juice extract, a leaf paraffin extract, and a leaf hydroglycerine extract.

3. The method of reducing loss of function of reproductive cells according to claim 2, further comprising the step of diluting said amount of said extract of *Hippophae*, said amount of said extract of *Hippophae* in a diluent effective upon contact with said reproductive cells to reduce loss of function.

4. The method of reducing loss of function of reproductive cells according to claim 3, further comprising the step of including an amount of an emulsifier in said diluent.

5. The method of reducing loss of function of reproductive cells according to claim 4, wherein said amount of said emulsifier comprises an amount of orvus paste.

6. The method of reducing loss of function of reproductive cells according to claim 3, further comprising the step of including an amount of egg yolk in said diluent.

7. The method of reducing loss of function of reproductive cells according to claim 3, further comprising the step of cooling said diluent which contains said amount of said extract of *Hippophae* to a temperature of between about 3° C. and about 30° C.

8. The method of reducing loss of function of reproductive cells according to claim 7, further comprising the step of freezing said diluent which contains said amount of said extract of *Hippophae*.

9. The method of reducing loss of function of reproductive cells according to claim 8, further comprising the step of thawing said diluent which contains said amount of said extract of *Hippophae*.

10. The method of reducing loss of function of reproductive cells according to claim 9, wherein said reproductive cells comprises at least one sperm cell.

11. The method of reducing loss of function of reproductive cells according to claim 10, wherein said at least one sperm cell is selected from the group consisting of: at least one bovine sperm cell, at least one equine sperm cell, at least one porcine sperm cell, at least one ovine sperm cell, and at least one avian sperm cell.

12. The method of reducing loss of function of reproductive cells according to claim 11, wherein said at least one sperm cell comprises a sex selected sperm cell.

13. The method of reducing loss of function of reproductive cells according to claim 10, wherein said step of combining said reproductive cells obtained from said animal with an amount of said extract of *Hippophae* effective upon contact with said reproductive cells to reduce loss of function comprises the step of combining said at least one sperm cell obtained from said animal with said amount of said extract of *Hippophae* effective upon contact with said at least one sperm cell to reduce loss of motility.

14. The method of reducing loss of function of reproductive cells according to claim 10, wherein said step of combining said at least one sperm cell obtained from said animal with said amount of said extract of *Hippophae* effective upon contact with said at least one sperm cell to reduce loss of function comprises the step of combining said at least one sperm cell obtained from said animal with said amount of said extract of *Hippophae* effective upon contact with said at least one sperm cell to reduce mortality.

15. The method of reducing loss of function of reproductive cells according to claim 10, wherein said step of combining said at least one sperm cell obtained from said animal with said amount of said extract of *Hippophae* effective upon contact with said at least one sperm cell to reduce loss of function comprises the step of combining said at least one sperm cell obtained from said animal with said amount of said extract of *Hippophae* effective upon contact with said at least one sperm cell to reduce loss of function due to oxidation.

16. The method of reducing loss of function of reproductive cells according to claim 9, wherein said reproductive cells comprises at least one oocyte.

17. The method of reducing loss of function of reproductive cells according to claim 16, wherein said at least one oocyte is selected from the group consisting of: at least one bovine oocyte, at least one equine oocyte, at least one porcine oocyte, at least one ovid oocyte, and at least one avian oocyte.

* * * * *